(12) United States Patent
Humphrey et al.

(10) Patent No.: US 10,161,863 B2
(45) Date of Patent: Dec. 25, 2018

(54) MEASUREMENT OF POROUS FILM (71) Applicant: NDC Technologies Limited, Essex (GB)

(72) Inventors: Kevin Paul Humphrey, Essex (GB); Robert Peter Hammond, Essex (GB)

(73) Assignee: NDC Technologies Limited, Essex (GB)

( * ) Notice: Subject to any disclaimer, the term of this patent is extended or adjusted under 35 U.S.C. 154(b) by 0 days.

(21) Appl. No.: 15/629,574

(22) PCT Filed: Dec. 18, 2015

(86) PCT No.: PCT/GB2015/054075
§ 371 (c)(1),
(2) Date: Jun. 21, 2017

(87) PCT Pub. No.: WO2016/102938
PCT Pub. Date: Jun. 30, 2016

(65) Prior Publication Data
US 2018/0024053 A1    Jan. 25, 2018

(30) Foreign Application Priority Data

Dec. 22, 2014 (GB) .................................. 1422964.5

(51) Int. Cl.
*G01N 21/47* (2006.01)
*G01N 21/35* (2014.01)
*G01N 21/84* (2006.01)
*G01N 9/24* (2006.01)
*G01N 15/08* (2006.01)
(Continued)

(52) U.S. Cl.
CPC ............. *G01N 21/47* (2013.01); *G01B 11/06* (2013.01); *G01N 9/24* (2013.01); *G01N 15/088* (2013.01);
(Continued)

(58) Field of Classification Search
CPC .. G01B 11/06; G01N 15/088; G01N 21/3563; G01N 21/359; G01N 21/57
See application file for complete search history.

(56) References Cited

U.S. PATENT DOCUMENTS

| 4,602,160 A | 7/1986 | MacTaggart |
| 4,755,678 A | 7/1988 | Izatt et al. |

(Continued)

FOREIGN PATENT DOCUMENTS

| EP | 2112498 A1 | 10/2009 |
| GB | 2127541 A | 4/1984 |
| WO | WO 2009/022126 A1 | 2/2009 |

OTHER PUBLICATIONS

Combined Search and Examination Report under Sections 17 and 18(3) for Great Britain Application No. GB1422964.5 dated Jul. 3, 2015.
(Continued)

*Primary Examiner* — Mark R Gaworecki
(74) *Attorney, Agent, or Firm* — Finnegan, Henderson, Farabow, Garrett & Dunner LLP (57) ABSTRACT

A method of calculating a first parameter of a first sample of a material is provided. The method includes determining a first and second wavelengths at which the material exhibits substantially no absorption; measuring a transmission of the first sample at the first wavelength; measuring a transmission of the first sample at the second wavelength; and calculating the first parameter of the first sample using a first multivariate regression model including first regression coefficients. The first parameter is a parameter which affects a total amount of radiation scattered by the first sample at the first and second wavelengths.

27 Claims, 5 Drawing Sheets

(51) Int. Cl.
*G01B 11/06* (2006.01)
*G01N 21/3563* (2014.01)
*G01N 21/86* (2006.01)
*G01N 21/3559* (2014.01)
*G01N 21/359* (2014.01)

(52) U.S. Cl.
CPC ....... *G01N 21/359* (2013.01); *G01N 21/3559* (2013.01); *G01N 21/3563* (2013.01); *G01N 21/8422* (2013.01); *G01N 21/86* (2013.01); *G01N 2015/086* (2013.01); *G01N 2015/0846* (2013.01)

(56) References Cited

U.S. PATENT DOCUMENTS

| | | |
|---|---|---|
| 5,087,817 A | 2/1992 | Chiba et al. |
| 5,124,552 A | 6/1992 | Anderson |
| 5,452,091 A | 9/1995 | Johnson |
| 5,568,400 A | 10/1996 | Stark et al. |
| 2003/0200040 A1 | 10/2003 | Trygg et al. |
| 2010/0032572 A1 | 2/2010 | Shelley et al. |

OTHER PUBLICATIONS

International Search Report for International Application No. PCT/GB2015/054075 dated Mar. 24, 2016.

Martens, Harald et al. "Light Scattering and Light Absorbance Separated by Extended Multiplicative Signal Correction. Application to Near-Infrared Transmission Analysis of Powder Mixtures," Analytical Chemistry, vol. 75, No. 3, Feb. 1, 2003, pp. 394-404.

Wang, Ke et al. "Multivariate Calibration of Near Infrared Spectroscopy in the Presence of Light Scattering Effect; A Comparative Study," School of Chemical and Biomedical Engineering, Nanyang Technological University, Published Mar. 31, 2011, pp. 1-16.

MEASUREMENT OF POROUS FILM

CROSS-REFERENCE TO RELATED APPLICATIONS

This is a U.S. National Phase of PCT/GB2015/054075, filed Dec. 18, 2015, which claims the benefit of priority to Great Britain Patent Application No. 1422964.5, filed Dec. 22, 2014, both of which are incorporated herein by reference.

FIELD

The present disclosure relates to a method of characterising a film. In particular, the present disclosure relates to a method of calculating a first parameter of a first sample of a material. More particularly, the present disclosure relates to a method of measuring the thickness, porosity and/or density of a porous film.

BACKGROUND

Microporous Lithium-ion battery separator film, "BSF", is typically polypropylene or polyethylene film between approximately 8-40 μm thickness, 5-25 g/m$^2$ mass per unit area, 0.5-0.65 g/cm$^3$ density.

Micropores in the film allow the propagation of charged ions between the cathode and anode of the battery. These micropores may not be uniformly distributed in the film. Therefore a film with uniform mass per unit area may still have significant variations in its density (and therefore thickness), depending on the distribution of micropores in the film.

Producers of BSF wish to know the variation of thickness, mass per unit area, density and/or porosity of film they are making across their production web, for quality assurance and production control purposes. The standard method for measuring the mass per unit area of polymer films on a moving web by infrared, X-ray, gamma ray or beta particles is to measure the transmitted radiation through the film and compare this to a standardised reading, taken with no film present. The heavier the film the less radiation is transmitted. The thickness of the film is then interpreted from the mass per unit area, by assuming that the film has a constant, uniform density. This causes unacceptable errors for any films that do not have uniform density across.

BSF does not have a uniform density because of micropores. Therefore, only an approximation of the thickness can be obtained using this method, rather than the true thickness. The more non-uniform the density of the film, the worse the approximation will be. It is also impossible to measure the density of the film using this method.

When infrared radiation interacts with microporous polymer film, some wavelengths are molecularly absorbed by the film. The wavelengths which are absorbed depend on the polymer. For example, polyethylene exhibits absorption centres around 2315, 2350 nm and between 3300-3600 nm. The snore polymer that is present, the more radiation is absorbed at these wavelengths. Therefore by measuring the amount of radiation transmuted through the film at the absorption wavelengths, information on the mass (mass per unit area) of the film can be ascertained.

Infrared radiation is also elastically scattered by the micropores in the film; the shorter the wavelength, the greater degree of scattering from the micropores. Short wavelengths (1500-2500 nm) are scattered more than longer ones (2500-5000 nm). The amount of scatter also depends on the number of micropores per unit volume (and hence the density of the film) and their morphology (size and shape). Porosity is a function of micropores quantity, size, and shape.

Scattering effects are therefore apparent as a continuous shift in the baseline in the near-infrared/mid-infrared, "NIR-MIR", spectrum, with the transmission of infrared, "IR", radiation directly through the BSF decreasing with shorter wavelengths. Low density BSF films have more micropores per unit volume and hence scatter IR to a greater degree. Therefore the lower the density the more pronounced the baseline change with shorter wavelengths. The resulting directly transmitted spectrum is therefore a combination of a continuous baseline variation, (which is a function of wavelength, film density and morphology of micropores in the film) and absorbance features (dependant on polymer type and mass per unit area of the film).

Figure 1:
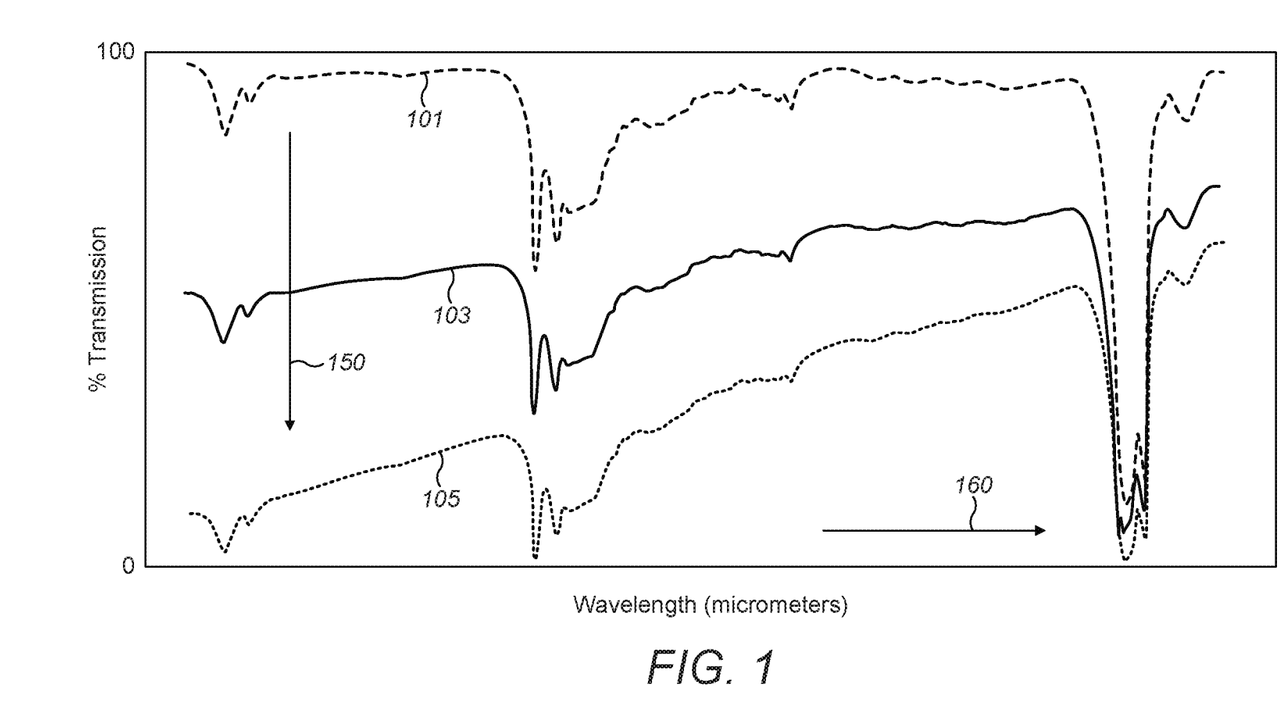
FIG. 1 shows transmission Spectra of polymer film with different scattering characteristics.

FIG. 1 shows example transmission spectra of polymer film with different scattering characteristics, but the same mass per unit area.

FIG. 1 shows three NIR-MIR transmission spectra: a first spectrum 101, a second spectrum 103 and a third spectrum 105. The first spectrum 101 is the NIR-MIR transmission spectrum obtained from a clear polymer film with no micropores. A second spectrum 103 is the NIR-MIR transmission spectra obtained from a second polymer film with micropores and therefore a lower density than the clear polymer film. A third spectrum 105 is the NIR-MIR transmission spectra obtained from a third film with a greater number of micropores and a lower density than the second polymer film. The chemical compositions of the three polymer films are identical and so the absorption peaks can be seen in the first spectrum 101, second spectrum 103 and third spectrum 105 at the same wavelengths.

A first arrow 150 indicates a first trend of increasing elastic scatter. As shown in FIG. 1, the proportion of NIR-MIR radiation scattered increases with decreasing film density. As also shown its FIG. 1, a second trend indicated by second arrow 160 also indicates a decrease in scatter with increasing wavelength. The second trend is attributed to the fact that scatter from micropores is more pronounced at shorter wavelengths in this region of the spectrum. This results in a baseline shift in the spectrum due to elastic scatter, dependant on wavelength; the slope of which depends on the number and morphology of the micropores in the film.

The current methods for measuring elastically scattering materials with NIR or MIR view baseline changes due to scattering effects as undesirable. Therefore these methods seek to remove it, so that the absorptions may be measured more effectively. This may be done by combining simultaneously measured transmission and diffuse reflectance spectra. See, for example, U.S. Pat. No. 4,602,160 which discloses a technique for measuring constituents in a moving paper web.

Alternatively, empirically-derived scattering models may be applied to the data in order to produce scatter-corrected spectra, such as multiplicative scatter correction (MSC) and extended multiplicative scatter correction (EMSC). See, for example, Journal of Anal. Chem 2003, 75, pp 394-404, and Anal. Lett. 2011, 44 pp 824-836 for an overall review.

Notably, previous methods focused on removing scattered-related features from the obtained spectra to improve measurement performance In contrast, the present disclosure describes methods for deriving useful information about, a sample from the scatter-related features which were previously discarded.

SUMMARY

Aspects of the present disclosure are defined in the appended independent claims.

There is provided an in-situ method of measuring properties of a moving porous film such as true thickness, porosity and density. The method uses measurements of the transmissivity of the porous film at a plurality of IR wavelengths at which the film exhibits substantially no absorption. The method therefore provides a measurement related to scattering. From this measurement, parameters of the porous film may be directly or indirectly determined.

There is further provided a method of combining this measurement with at least one further measurement at an absorbing wavelength to further characterise the porous film.

There is also provided another method of determining parameters of the porous film by an alternative use of parameters from scatter correction models.

Methods in accordance with the present disclosure purposely use the IR spectrum baseline variation resulting from elastic scatter effects, during measurement of a moving polymer web to obtain information on the film's density and/or porosity. Usually this information is discarded during pre-treatment of the spectrum in order to remove scatter effects because scatter is seen as introducing an error into absorption measurements.

The inventors recognised that the baseline may be used to obtain information on scattering from BSF micropores and hence information on the density of a BSF. Optionally, by combining this with IR transmission information measured at the absorption wavelengths si is possible to construct a true thickness, mass per unit area and density measurement.

Conventionally, regression methods such as partial least squares are applied over an entire spectrum. Multivariate regression to transmitted light at specific scattering wavelengths is not a known procedure.

Notably, the improved method in accordance with the present disclosure allows a BSF manufacturer to accurately measure the cross-web thickness, density and porosity profile of a moving BSF polymer web in-situ. This enables the manufacturer to dynamically control their production process based on the in-situ thickness, density or porosity profiles during a production run. The production control assists the manufacturer in producing film that has uniform thickness, density and porosity which are key quality parameters for good BSF.

Current established technology for measuring BSF such as X-ray or nuclear gauges can only measuring the in-situ mass per unit area cross-web profile. Therefore dynamic control based on these profiles may only assist in producing films of uniform mass per unit area, which still may still have non uniform thickness, density and porosity.

Advantageously, the method may be employed in-situ using a measurement gauge arranged to probe a sample at only a relatively small number of discrete wavelengths. In fact, in accordance with the present disclosure, a porous sample may be fully characterised in situ using only three wavelength measurements. Notably, a full spectrum gauge is not essential—although it may be used.

Nuclear and X-ray measurement gauges are conventionally used to measure parameters of BSFs. In general, infrared measurement gauges are advantageous over nuclear gauges and X-ray for at least the following reasons:
  safer (unlike beta and x-ray, infrared radiation is non-ionising radiation);
  no need for extra precautions/legal obligations that would be necessary with ionising radiation e.g. setting up restricted areas around gauges, specialist training of operators, beta gauge source storage, transport and disposal;
  nuclear (e.g. beta) sources lose their activity over time— for example, Pm147 has a half life of 2.6 years which means these gauges that get nosier over time—there is no similar drop off in infrared gauge performance;
  infrared measurement gauges are less sensitive to environmental factors such as air temperature and pressure or humidity—there is therefore no need to perform periodic air standardisations or have dry/constant temperature air purges; and
  much wider air gap (space between transmission and detection heads) allowed for IR gauges (appox. 8 cm) c.f. 1 cm for beta or 2 cm for x-ray. This makes it easier to thread web between gauges heads during line start up—also less likely for web to foul beads during production.

The present disclosure provides new methods of using measurements from an infrared measurement gauge which make this device a viable alternative to nuclear and X-ray measurement gauges There is disclosed herein a gauge that measures scatter from micropores as well as true thickness and density. Advantageously, the infrared measurement gauge in accordance with the present disclosure can measure film with a wide range of densities without requiring different calibration settings to be loaded into the gauge. A true measurement of the thickness (and hence a measurement of density/ porosity) is possible by measuring the extent of the pores in the film. The inventors have recognised that this is possible with an infrared measurement gauge. X-rays and beta waves are not scattered by the pores so simply cannot make these measurements.

BRIEF DESCRIPTION OF DRAWINGS

Embodiments of the present disclosure will now be described with reference to the accompanying drawings in which.

In the figures, like reference numerals refer to like parts.

DETAILED DESCRIPTION OF THE DRAWINGS

The term "parameter" is used to denote a property such as thickness, porosity, density, or mass per unit area. The term "sample" is used to denote a specific target which is being measured. The sample may have some known and some unknown parameters. The term "material" is used to refer to the composition of the sample such as the chemical and structural composition.

In accordance with the present disclosure, near-infrared, "NIR", may be considered to be wavelengths generally in the range 1-2.5 µm and mid-infrared, "MIR", may be considered to be wavelengths generally in the range 2.5-5 µm.

Infrared absorption gauges are used for measuring various constituents or parameters of samples, such as the moisture content of the sample, the thickness or coating weight of a film on a base layer or substrate, or the thickness or basis weight (mass per unit area) of the sample.

Infrared absorption gauges conventionally operate by projecting infrared radiation onto a sample and measuring the intensity of the radiation diffusely reflected, transmitted and/or scattered-by the sample.

Signals proportional to the measured intensity are processed to provide values of the parameters being measured.

A distinction may be drawn between a first category of gauge which probes a sample over a continuous spectrum of wavelengths in a region, such as NIR-MIR region, and a second category of gauge which probes a sample at only a plurality of discrete wavelengths which have been carefully selected. It may be understood that the first category of gauge may be considered a continuous spectrum device. The first category of gauge is generally larger and more expensive than the second category of gauge. The second category of gauge may be distinguished from the first category of gauge by the feature that there is a selection of specific wavelengths. This selection is generally based on the material and/or optical properties of the sample. The second category of gauge may implement a plurality of narrow bandwidth optical filters to respectively "select" radiation at the plurality of predetermined wavelengths. Embodiments relate to the second category of gauge. Advantageously, the inventors have found that good BSF measurements can be made with a small number of predetermined wavelengths, allowing low cost gauges of the second category to be used which is more cost effective.

In embodiments, the wavelengths projected by the gauge are chosen based on the material of interest. In embodiments, wavelengths are chosen at which the material exhibits different optical behaviour. In embodiments, a first wavelength may be chosen at which the sample exhibits a relatively low degree of absorption and a second wavelength may be chosen at which the sample exhibits a relatively high degree of absorption. For example, when measuring the amount of water in a sample, one of the wavelengths can be chosen at an absorption wavelength of water (either 1450 nm or 1945 nm) and the other wavelength may be a "reference wavelength" which is chosen to be one that is not significantly absorbed by water.

The gauge includes an infrared radiation source (for example, a filament lamp) having a constant emission spectrum, and a detector for receiving radiation reflected, transmitted and/or scattered by the sample. Optionally, a reference detector may also be used. In embodiments, the narrow bandwidth filters are placed between the source and the sample to expose the sample only to the desired measuring and reference wavelengths, in this case, the sample is successively exposed to radiation at the selected wavelengths, e.g. by placing appropriate filters on a rotating wheel in front of the radiation source. In other embodiments, the filter wheel is placed between the sample and the detector, and each filter is successively interposed between the sample and the detector. Other ways of measuring film using the second category of gauge are known and are equally compatible with the present disclosure.

The detector measures the intensity of light after interaction with the sample and produces a signal according to the intensity of the radiation incident upon it. In the simplest case, by calculating the ratio between the signal from the detector when receiving light at the measuring wavelength and the signal from the detector when receiving light at the reference wavelength, a measurement signal can be obtained that provides a measure of a parameter. Several measuring wavelengths and/or several reference wavelengths may be used, and the signals of the measuring wavelengths and of the reference wavelengths used to calculate the parameter concerned.

The present disclosure provides a method for measuring the thickness, porosity, density and/or mass per unit area of a porous sample. In advantageous embodiments, the porous sample is a BSF, such as a Lithium-ion BSF, formed on a moving production line as a BSF web. In embodiments, transmitted infrared light is measured on a moving BSF web. However, it may be understood that the present disclosure is not limited to the method by which the BSF is produced. Likewise, embodiments relate to a BSF by way of non-limiting example only. Methods in accordance with the present disclosure are equally applicable to any film that elastically scatters, such as breathable film, voided (pearlised) film or film that contains additives or fillers that scatter IR radiation.

In overview, the present disclosure relates to using baseline shifts present in the spectrum (or present over several discreet wavelengths) due to scatter to measure the scatter characteristics of pores.

Figure 2:
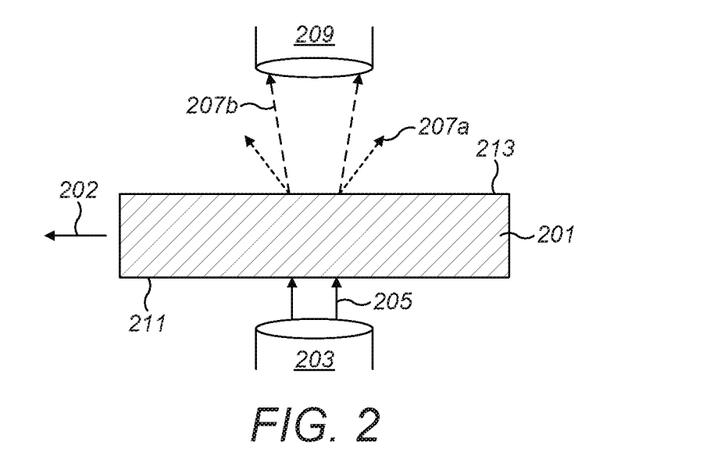
FIG. 2 illustrates IR radiation transmitted through a moving web of BSF.

FIG. 2 shows an embodiment of the present disclosure.

There is shown a NIR-MIR light engine, or transmitter, producing a nominally collimated beam of infrared light which is shone on a moving battery film web. The transmitted light is then detected by a receiver. In FIG. 2, the light is shone from beneath the web, but the positions of the transmitter and receiver may be swapped.

More specifically, FIG. 2 shows a cross-section of a battery separator film 201, a NIR-MIR light transmitter 203 and NIR-MIR light receiver 209. The NIR-MIR light transmitter 203 and NIR-MIR light receiver 209 are arranged either side of the plane of the battery separator film 201. The NIR-MIR light transmitter 203 is arranged to irradiate the battery separator film 201 and the NIR-MIR light receiver 209 is arranged to receive light from the NIR-MIR light transmitter 203 which is transmitted by the battery separator film 201.

FIG. 2 shows she difference in scatter of transmitted IR radiation from the battery separator film at different wavelengths. Relatively short wavelength light 207a is generally highly scattered and only a small proportion is collected by the receiver. Relatively long wavelength light 207b is by contrast scattered to a lesser extent, hence a larger proportion is detected by the receiver as being transmitted through the film.

More specifically, in operation, the NIR-MIR light transmitter 203 produces a collimated beam 205 of NIR-MIR light. In this embodiment, the optical axis of the collimated beam 205 is substantially orthogonal to the plane of the battery separator film 201. However, in other embodiments, the optical axis of the collimated beam 205 is not substantially orthogonal to the plane of the battery separator film 201. The collimated beam 205 is incident on a first surface 211 of the battery separator film 201. The collimated beam 205 is scattered by the battery separator film 201. As shown in FIG. 2, relatively short wavelength light 207a is scattered more than relatively long wavelength light 207b. The scattered light 207a, 207b emerges from a second surface 213 of the battery separator film 201. A NIR-MIR light receiver 209 receives light emerging from the second surface 213 of the battery separator film 201. Although embodiments describe a specific optical arrangement for obtaining the transmitted IR spectrum, methods described below for determining parameters of the sample are not limited to the optical arrangement used to obtain the transmitted IR spectrum. That is, for the purposes of the methods described below, it does not matter how the transmitted IR spectrum is obtained.

The methods described below may be used to process data from any type of gauge including the first category of gauge and the second category of gauge. In embodiments, the methods described below are applied to a reduced spectrum, consisting of only a relatively small number of wavelengths generated by using pre-specified IR filters mounted on a spinning filter wheel or in any other suitable arrangements in the light engine. Alternatively, the continuous NIR-MIR spectrum can be used, obtained through a measurement technique such as (for example) Fourier transform infrared spectroscopy (FT-IR).

Broadly speaking, two methods of using IR elastic scatter to measure a parameter, such as true thickness, of a BSF are described below. In both cases, the BSF pore size and morphology is assumed to be approximately constant, but the density of the film (number of micropores per unit volume) is varying.

Multivariate Regression on Scatter-Affected Wavelength—"Method 1"

In summary, various wavelengths of IR transmitted light in regions of the spectrum that are known to be sensitive to elastic scatter in the BSF are measured (i.e. in regions of the spectrum where baseline changes are most prevalent). The regions are also selected so they do not contain absorption features characteristic of the polymer than makes up the BSF. The transmission of the sample is measured at these wavelengths. Optionally, several ratios of the transmission at these wavelengths are then calculated. Using these measurements or ratios, the baseline changes due solely to elastic scatter in these areas of the IR spectrum can be measured. In embodiments, the measurements or ratios of the measurements are used as predictors in a curve fitting or multivariate linear regression model.

In an embodiment, a ratio is calculated by dividing the measurement of transmission at a non-absorbing, scatter-affected wavelength by the measurement of transmission at a non-absorbing, scatter-unaffected wavelength.

More specifically, there is provided a method for determining as unknown first parameter of a first sample of a material using measurements of the IR transmission of the first sample at a plurality of wavelengths. The first parameter is related or linked (e.g. by a simple linear proportional or polynomial relationship) to porosity, density and/or thickness. In embodiments, the first parameter is a parameter which affects the amount or degree of scattering exhibited at the plurality of wavelengths. In yet further alternative embodiments, the first parameter is a scatter-related parameter calculated from regression of the absorption wavelengths to thickness (or alternatively density or porosity). In embodiments, the first parameter is porosity, density and/or thickness.

To scatter, the wavelength needs to be of approximately the same order as the pore size. By way of non-limiting example only, BSF typically contains pores with a size of approximately 30-1000 nm. In some BSF, features larger than this may be included which also usefully scatter IR light (depending on morphology). In embodiments, the material of interest comprises pores having a diameter greater than approximately 30 nm. In embodiments, wavelengths used by the gauge (including the first and second wavelengths) are in the MIR-NIR region. In embodiments, the wavelengths are selected from within the range 1500-5000 nm. By way of contrast, a typical X-ray sensor has wavelengths ~0.1 nm which are too short to scatter from any pores regardless of morphology.

The method comprises firstly determining at least two wavelengths at which the material exhibits substantially no absorption. The two wavelengths will exhibit different degrees of scattering became the degree of scattering is wavelength dependent. The IR transmission of the first sample is measured at the at least two wavelengths. These measurements are used in a multivariate regression equation with known regression coefficients to calculate the first parameter.

The skilled person understands how to use a multivariate regression equation comprising known regression coefficients to determine a dependent variable of the multivariate regression equation. However, for completeness, embodiments are described below by way of a non-limiting example only.

In an embodiment, the multivariate regression equation is:

$$\alpha_1 \ln T1 + \alpha_2 \ln T2 + \ldots + \alpha_i \ln Ti + C = S \tag{1a}$$

wherein: $\alpha_1, \alpha_2, \ldots, \alpha_n$ are the regression coefficients, T1, T2, ..., Ti are either the respective transmission measurements at the first, second, . . . and ith wavelengths or ratios of the transmission measurements at the first, second, . . . and ith wavelengths, C is a constant offset; and S is the first parameter of the first sample.

The regression coefficients $\alpha_1, \alpha_2, \ldots, \alpha_i$ are dependent on the composition, micropore pore size and micropore morphology of the sample and the optical design of the gauge. In embodiments described below, the regression coefficients are determined empirically through a calibration process. In alternative embodiments, the regression coefficients are obtained from a look-up table.

Again, although embodiments relate to a specific multivariate regression equation, it may be understood that other multivariate regression equations may be suitable depending on the application.

In another embodiment, the multivariate regression equation is:

$$\alpha_1 \cdot T1 + \alpha_2 \cdot T2 + \ldots + \alpha_i \cdot Ti + C = S \tag{1b}$$

where $\alpha_1, \alpha_2, \ldots, \alpha_i$ are the regression coefficients; T1, T2, ..., Ti are ratios of the transmission measurements at the first, second, . . . and ith wavelengths; C is a constant offset; and S is the first parameter of the first sample.

In a yet further embodiment, the multivariate regression equation is:

$$\alpha_{11} \cdot T1 + \alpha_{21} \cdot T2 + \ldots + \alpha_{12} \cdot (T1)^2 + \alpha_{22} \cdot (T2)^2 + \ldots + \alpha_{13} \cdot (T1)^3 + \alpha_{23} \cdot (T2)^3 + \ldots + \alpha_{ij} \cdot (Ti)^j + C = S \tag{1c}$$

where $\alpha_{11}, \alpha_{21}, \ldots, \alpha_{ij}$ are the regression coefficients; T1, T2, ..., Ti are ratios of the transmission measurements at the first, second, . . . and ith wavelengths, C is a constant offset; and S is the first parameter of the first sample.

In another embodiment, the multivariate regression equation is:

$$\alpha_1 \cdot T1 + \alpha_2 \cdot T2 + \ldots + \alpha_{11} \cdot (T1)^2 + \alpha_{22} \cdot (T2)^2 + \ldots + \alpha_{12} \cdot (T1) \cdot (T2) + \ldots + \alpha_{ij} \cdot (T_i)(T_j) + C = S \tag{1d}$$

where $\alpha_{11}, \alpha_{21}, \ldots, \alpha_{ij}$ are the regression coefficients; T1, T2, ..., Ti are ratios of the transmission measurements at the first, second, . . . and ith wavelengths; C is a constant offset, and S is the first parameter of the first sample.

In further embodiments, the multivariate regression equation is a mixture of the above equations—e.g. S=(Eqn 1a)+(Eqn 1d). Again, the skilled person will understand how a multivariate regression equation comprising known regression coefficients to determine a dependent variable.

There is therefore provided a method of calculating a first parameter, S, of a first sample of a material, the method comprising: determining a first and second wavelength at which the material exhibits substantially no absorption, measuring the transmission of the first sample at the first wavelength; measuring the transmission of the first sample at the second wavelength; calculating a first parameter of the first sample using a first multivariate regression model comprising first regression coefficients, wherein the first parameter is a parameter which affects the total amount of radiation scattered by the first sample at the first and second wavelengths.

In an embodiment, the step of measuring the transmission of the first sample at the first wavelength comprises illuminating the first sample with incidence radiation including the first wavelength and measuring the intensity of radiation transmitted by the first sample at the first wavelength. Likewise, in an embodiment, the step of measuring the transmission of the first sample at the second wavelength comprises illuminating the first sample with incidence radiation including the second wavelength and measuring the intensity of radiation transmitted by the first sample at the second wavelength.

In an embodiment, the method is performed using a second category of gauge. It may therefore be understood that, in an embodiment, the step of measuring the transmission of the first sample at the first wavelength comprises filtering radiation at the first wavelength and/or the step of measuring the transmission of the first sample at the second wavelength comprises filtering radiation at the second wavelength. However, it may be understood that methods described herein are equally applicable to the first category of gauge.

The filtering may be performed on the incident radiation or the transmitted radiation. Therefore, in an embodiment, the step of filtering radiation at the first wavelength is performed on radiation incident on the first sample and/or radiation transmitted by the first sample at the first wavelength. Likewise, in an embodiment, the step of filtering radiation at the second wavelength is performed on radiation incident on the first sample and/or radiation transmitted by the first sample at the second wavelength.

Embodiments described NIR-MIR light; and NIR-MIR light transmitters and receivers by way of non-limiting example only. The method disclosed for determining a sample parameter which affects the total amount of radiation scattered is equally suitable to other parts of the electromagnetic spectrum provided the sample of interest exhibits wavelength-dependent scattering in that part of the electromagnetic spectrum.

In an embodiment, the first and second wavelengths are visible and/or infra-red wavelengths, optionally, near-infrared and/or mid-infrared wavelengths. However, it may be understood that, the disclosed methods may be employed using measurements in other bands of the electromagnetic spectrum. That is, the present disclosure is not limited to BSF and NIR-MIR measurements.

In an embodiment, the transmission is measured at two wavelengths. In an embodiment, the sample scatters the incident radiation at only one of the two wavelengths. That is, in an embodiment, at least one of the first and/or second wavelengths are scatter-affected wavelengths. In another embodiment, the sample scatters the incident radiation at both wavelengths but the amount of scatter exhibited by the first sample at the first wavelength is different to the amount of scatter exhibited by the first sample at the second wavelength. Optionally, the transmission may be measured at additional wavelengths.

Again, the first parameter may be any parameter of the sample which affects the amount of light scattered by the sample. It may be understood that the regression coefficients are determined, or calculated, based on the first parameter.

It may be understood that a variety of different models may be appropriate for determining the first parameter and the present disclosure is not limited to the specific models described. The model needs to provide a measure of the baseline slope. In an embodiment, the first multivariate regression model is a first linear multivariate regression model.

In an embodiment, the regression coefficients are calculated by a prior calibration method. A training set of battery film samples with known thicknesses, mass per unit areas and densities may be used to generate regression coefficients. The response variable (first parameter) is a quantity that depends on the elastic scatter in the moving web, which may be the density of the film sample, or an expected scatter factor, calculated from the known thickness and mass per unit area of the sample.

In an embodiment, the method further comprises calculating the first regression coefficients by: measuring the transmission of a second and a third sample of the material at the first wavelength, measuring the transmission of the second and the third samples at the second wavelength; measuring the respective first parameters of the second and third samples; and calculating the first regression coefficients of the first multivariate regression model, wherein the transmissions measurements of the second sample at the first and second wavelengths are the independent variables and the corresponding first parameter measurement of the second sample is the dependent variable of a first equation of the first multivariate regression model, and wherein the transmissions measurements of the third sample at the first and second wavelengths are the independent variables and the corresponding first parameter measurement of the third sample is the dependent variable of a second equation of the first multivariate regression model.

These optional steps for calculating the regression coefficients notably include the step of measuring the first parameter of at least a second and third sample of the material. The second and third samples may be referred to as "calibration" samples, or the "training set", because the value of the first parameter for these samples is known. The method employed for measuring the first parameter depends on the nature of the first parameter.

The skilled person will understand how to solve the regression equations to determine the regression coefficients. If two wavelength ratios are used for the method, there will be two regression coefficients and a constant offset (see equation 1) and therefore three calibration samples having a measured value of the first parameter will be required. That is because at least three equations are required to determine three unknowns (the regression coefficients and constant offset). In practice, a larger number of calibration samples may be used.

In an embodiment, the first parameter, S, is porosity and the step of measuring the first parameter, S, of the second and/or third sample comprises calculating the porosity of the second and/or third sample using the formula, $$1-(\text{sample density/material density}) \quad (2)$$

wherein "sample density" is the density of the sample, measured by dividing the mass per unit area of the sample by the sample thickness, and "material density" is the known density of the material with no pores. Porosity may be quoted as a percentage.

In another embodiment, the first parameter, S, is thickness and the step of measuring the first parameter of the second and/or third sample comprises measuring the thickness of the second and/or third sample using a micrometer, optionally, a contact micrometer.

The first and second wavelengths are wavelengths at which the material exhibits substantially no absorption. These wavelengths may be identified from previously obtained data or prior knowledge of the material. In embodiments, the first and second wavelengths are determined by spectroscopy. Specifically, the first and second wavelengths may be determined by identified regions of the spectra without absorption peaks. The skilled person will understand how to identify suitable first and second wavelengths, and the present disclosure is not therefore limited to particular wavelengths.

Multivariate Regress on Absorption Affected Wavelengths

A similar method may be used to determine a second parameter of a sample using at least one absorption affected wavelength.

In summary, regions of the spectrum which contain absorption wavelengths of the BSF polymer but a low degree of baseline shift due to scatter may also be used as predictors in a multivariate regression model, using the same training set. The response variable (the second parameter of the sample) may be the mass per unit area of the film sample, or an expected absorption factor, based on the known thickness and mass per unit area of the sample.

In an embodiment, the response variable is the thickness (or alternatively the density or porosity) of the sample, in the knowledge that the resultant regression will not give an accurate result (because it is based on absorption wavelengths), but the resulting errors in the predicted thickness for each sample by the model when compared to the actual thickness can be used to calculate S, the necessary correction required to the accurately measure thickness. The correction factor may be used as the first parameter in the regression equation for the scattered-affected wavelengths.

In an embodiment, the method further comprises calculating a second parameter, A, of the first sample using a second multivariate regression model comprising second regression coefficients, wherein the second parameter is a parameter related (e.g. by a simple linear proportional or polynomial relationship) to the mass per unit area, g/m², of the first sample. In embodiments, the second parameter is the mass per unit area of the first sample. The second parameter may be related or linked to mass per unit area in any number of ways and the present disclosure is not limited to the embodiments in this respect.

The method comprises firstly determining at least two wavelengths at which the material exhibits different degrees of absorption. For example, one wavelength (a "third wavelength") may be a wavelength at which the sample exhibits no absorption and the other wavelength (a "fourth wavelength") may be a wavelength at which the sample exhibits a relatively large amount of absorption. As per the earlier method, additional wavelengths may be used to increase the accuracy of the model. The IR transmission of the first sample is measured at these at least two further wavelengths. These measurements are used in a second multivariate regression equation with known second regression coefficients to calculate the second parameter.

In an embodiment, the method therefore further comprises: determining a third and fourth wavelength, wherein the amount of absorption exhibited by the first sample at the third wavelength is different to the amount of absorption exhibited by the first sample at the fourth wavelength; measuring the transmission of the first sample at the third wavelength including filtering radiation at the third wavelength; and measuring the transmission of the first sample at the fourth wavelength including filtering radiation at the fourth wavelength.

In an embodiment, the third and fourth wavelengths are in a region of the spectrum where baseline-shift due to scatter is relatively low.

Again, the skilled person understands how to use a multivariate regression model comprising known regression coefficients to determine a dependent variable of the multivariate regression equation. Multivariate regression equations of the type shown in equation 1 are suitable.

In an embodiment, the second multivariate regression equations take the form:

$$\beta_1 \ln T1 + \beta_2 \ln T2 + \ldots + \beta_n \ln Tn + C = A \quad (3)$$

wherein: $\beta_1, \beta_2, \ldots, \beta_n$ are the second regression coefficients, T1, T2, ..., Tn are the respective transmission measurements at the first, second, ... and ith wavelengths; C is a constant offset and A is the second parameter of the first sample.

The second regression coefficients $\beta_1, \beta_2, \ldots, \beta_n$ are dependent on the composition of the sample. In embodiments described below, the second regression coefficients are determined empirically through a calibration process. In alternative embodiments, the second regression coefficients are obtained from a look-up table.

For an absorption wavelength, the transmitted radiation T1 is given theoretically by the Beer-Lambert law: this states that if $T1_{incident}$ is the incident radiation at wavelength 1 then, $T1 = T1_{incident} \exp(-kG)$, where k is an absorption constant depending on the material and wavelength and G is the sample mass per unit area. Therefore if absorption is the only loss of infrared radiation then equation 3 (i.e. a log) advantageously provides a linear response.

Again, although embodiments relate to a specific multivariate regression equation, it may be understood that other multivariate regression equation, such as those shown in equations 1b to 1d, are suitable. Again, the skilled person will understand how to solve the regression equations to determine the regression coefficients.

The second regression coefficients may likewise be calculated by a prior calibration method. In an embodiment, the method further comprises calculating the second regression coefficients by: measuring the transmission of a fourth and a fifth sample of the material at the third wavelength; measuring the transmission of the fourth and the fifth samples at the fourth wavelength, measuring the respective second parameters of the fourth and fifth samples; and calculating the second regression coefficients of the second multivariate regression model, wherein the transmissions measurements of the fourth sample at the third and fourth wavelengths are the independent variables and the corresponding second parameter measurement of the fourth sample is the dependent variable of a first equation of the second multivariate regression model, and wherein the transmissions measurements of the fifth sample at the third and fourth wavelengths are the independent variables and the corresponding second parameter measurement of the fifth sample is the dependent variable of a second equation of the second multivariate regression model.

These optional steps for calculating the second regression coefficients notably include the step of measuring the second parameter of at least a fourth and fifth sample of the material. The fourth and fifth samples may be referred to as "calibration" samples, or the "training set", because the value of the second parameter for these samples is known. The method employed for measuring the second parameter depends on the nature of the second parameter.

In an embodiment, the second parameter is "grammage" or mass per unit area, g/m$^2$, and the second parameter of the fourth and fifth samples are measured by weighing samples of a known area.

In an advantageous embodiment, the third or fourth wavelength is the same as the first or second wavelength. In a further advantageous embodiment, the fourth and/or fifth samples are the same as the second and/or third samples. These embodiments are advantageous because the amount of calibration and/or the number of calibration measurements required are reduced.

In an embodiment, the reference thicknesses of the samples are regressed to absorption wavelengths. The predicted values from this regression could be compared against the actual thickness reference values—from this a scatter value for each sample could be calculated. This is then the "first parameter" which would be regressed to scattered wavelengths.

Combining Outputs from the Two Multivariate Regression Models

Figure 3:
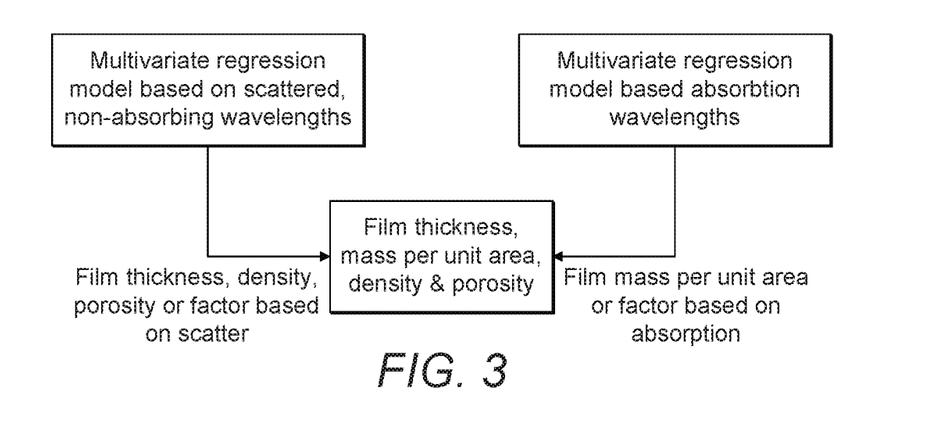
FIG. 3 shows a combination of scatter and absorption models in accordance with embodiments.

The two regression models may then be combined in a subsequent calculation, to obtain thickness, mass per unit area and density of the BSF. This is shown in FIG. 3.

In an embodiment, the method further comprises combining the calculated first parameter, S, of the first sample with the calculated second parameter, A, of the first sample to calculate at least one of the following further parameters of the first sample: thickness, mass per unit area, density and porosity.

This combination can take the form of a simple multiplication or division. For example if the scattering model gives the density and the absorption model the mass per unit area, the combination function is a multiplication of the two to obtain true thickness. That is, in an embodiment, the combining is simple multiplication or simple division, if the first parameter is thickness and/or the second parameter is mass per unit area.

Otherwise the combination function may involve other mathematical operations to obtain thickness, mass per unit area and density, depending on how the expected scatter and absorption motors were calculated from the training set thicknesses and mass per unit areas.

Additionally this model may be extended to encompass BSF with notably different scattering morphologies by incorporating the regression coefficients for each model themselves in a combination function—for example, by adding the scatter and absorption coefficients as a weighted sum. This combination will be made based on another training set of samples that have the different morphology.

In an embodiment, the step of combining the calculated first parameter with the calculated second parameter comprises calculating the thickness, mass per unit area, density or porosity, T, of the first sample using a product equation:

$$T=a[(Sb+c)(Ad+e)]+f \quad (4a)$$

where S is any scatter based output from the scatter-affected wavelengths model, A any absorption based output from the absorption-affected wavelengths model, and a, b, c, d, e and f are empirically-calculated constants.

Other ways of combining the scatter and absorption parameters are equally suitable. In alternative embodiments, the product equation is:

$$T=a[(Sb+c)/(Ad+e)]+f \quad (4b)$$

or $$T=a[(Ad+e)/(Sb+c)]+f \quad (4c)$$

In embodiments, the offsets may be zero. In embodiments using six offsets, at least six calibration samples are used. In embodiments, more than six calibration samples are used.

In one example, wherein the first parameter is density, the second parameter is mass per unit area and the further parameter is thickness, and the step of combining the calculated first parameter with the calculated second parameter comprises calculating the thickness, T, of the first sample using a product equation:

$$T=a\{A[(Sb)+c]\}+d \quad (4d)$$

Again, where a, b, c and d are empirically-determined constants.

These equations are provided by way of non-limiting example only and it may be understood that other mathematic combinations of the scatter and abortion parameters are possible.

In embodiments, the first parameter is a parameter which, when mathematically combined with a parameter affected by the absorption of the sample (i.e. a "second" parameter as referred to herein) provides a measure of the porosity or density or thickness. In embodiments, the second parameter is an estimation of porosity or density or thickness determined from a regression model on absorption affected wavelengths, which requires combination with the output from a regression model based on scatter-affected wavelengths to provide a true measure of porosity or density or thickness.

In an example, the first parameter is calculated by performing the following steps: (1) take samples of a known thickness (or porosity or density); (2) make a regression of thickness (or porosity or density) to absorption wavelengths—from this calculate the absorption regression coefficients and also the predicted thickness values for each sample; (3) use equation 4 (or an alternative method to combine the parameters) in reverse, to calculate the first parameter that is required for each sample in order for the predicted thickness (or porosity or density) from the absorption wavelength model (after combination using equation 4 to read the correct thickness; and (4) take the calculated scatter parameter from step 3 and make a regression of this to scatter wavelengths (from this calculate the scatter-regulated regression coefficients).

Alternative Method for Making Measurements Based on Scatter-Affected Wavelengths—"Method II"

In an embodiment, an alternative method is employed for measuring the extent of scatter in the sample. This method is an alternative to the method of multivariate regression on scatter-affected wavelengths, Method I, described above. The output of this method may be combined with the multivariate regression on absorption-affected wavelengths in the same way as described above.

The method is based on multiplicative scatter correction, "MSC" but the same principle can be used with other scatter correction models, such as extended multiplicative scatter correction (EMSC), inverted scatter correction (ISC), extended inverted scatter correction (EISC), standard normal variate (SNV) and optical path length estimation and correction (OPLEC). These techniques may usually be employed with the first category of gauge however, in embodiments, Method II is used with measurements from the second category of gauge (i.e. a series of measurement taken at discrete wavelengths).

MSC assumes that scatter effects can be modelled as deviations from a 'typical' absorption spectrum. The absorption spectrum (A) of a sample of battery film may be obtained from its transmission (T) spectrum by the transform $A=\ln(1/T)$. The 'typical' spectrum (m, expressed as a vector) can be approximated from averaging the absorption spectra of many different samples of BSF, or can be a rolling average spectrum—for example, of a moving BSF web measured over time. Any one spectral measurement $X_i$ (where i is the sample number and X the absorption spectrum) can then be approximated as:

$$X_i \sim a_i + b_i \times m \quad (5)$$

Therefore by linear regression of $X_i$ to the average 'typical' spectrum m, parameters $a_i$ and $b_i$ can be estimated. In conventional MSG, the spectrum is then corrected to remove the unwanted scatter effects using the equation:

$$X_{con} = (X_i - a_i)/b_i \quad (6)$$

In summary, instead of using MSG to remove scatter, the multiplication coefficient $b_i$ is taken as a measure of the extent of the scatter in the BSF. The parameter $b_i$ can therefore be used to measure the film sample's thickness and/or density—either directly or, as per above, combined with a conventional measurement of the sample's mass per unit area, based on absorbing features in areas of the spectrum.

That is, in embodiments, MSC scatter correction parameters are used to quantify (rather than just correct for) scatter in a moving web.

In an embodiment, the parameter b is found from the slope of an x-y chart which plots the spectrum of the sample being measured ($X_i$, at least two wavelengths) against an average set of archive spectra (m). In this embodiment, parameter b is simply a measure of slope of the spectrum (due to scatter) of the sample being measured.

It may therefore be understood that b is a parameter which reflects now much light is scattered by the sample. That is, like scattering parameter S described above, parameter b is also related to thickness, porosity and/or density. Accordingly, parameter b may fee related to S through a simple linear or polynomial relationship. In embodiments, parameter b is used as a substitute for S.

In a further embodiment, MSC is extended (EMSC) by including prior knowledge of the absorption spectrum of each sample of BSF to be measured. In this embodiment, a hypothetical absorption spectrum of each sample with no scatter is modelled. This is done by using the absorption spectrum (measured on the same gauge) of an non-scattering sample of the polymer the BSF is made from with a known mass per unit area and no micropores. This is then scaled by the mass per unit area of the BSF sample being measured, this mass per unit area value obtained by measurement of absorbing features in areas of the spectrum known not to be affected by scatter. There is therefore provided an alternative method of calculating a first parameter, S, of a first sample of a material, the method comprising: determining the typical spectrum for a sample of the material; obtaining a spectrum of the first sample; quantifying the deviation of the obtained spectrum from the average spectrum; and using the quantified deviation as a measure of tire first parameter, S.

In an embodiment, the step of determining a typical spectrum of the material comprises averaging the measured spectra of a plurality of samples of the material, optionally, by employing a rolling time average measurement of the spectrum measured on a moving sample of the material. In an embodiment, the moving sample is a moving web of BSF.

The "typical spectrum" may also be described as being an "average spectrum". In an embodiment, the typical spectrum also includes a spectrum of a non-scattering sample of the same polymer material, scaled according to the known mass per unit area of the first sample, to model the absorption wavelengths. In an embodiment, the step of quantifying the deviation comprises obtaining scatter correction parameters by comparison of the typical spectrum with the spectrum of the first sample. In an embodiment the step of using the quantified deviation comprises using the scatter correction parameters that would normally be used to correct for scatter and then discarded, to instead quantity the first parameter, S.

An alternative embodiment uses $a_i$, the offset to measure scatter S—either on its own or in conjunction with $b_i$.

Example Results

Figure 4:
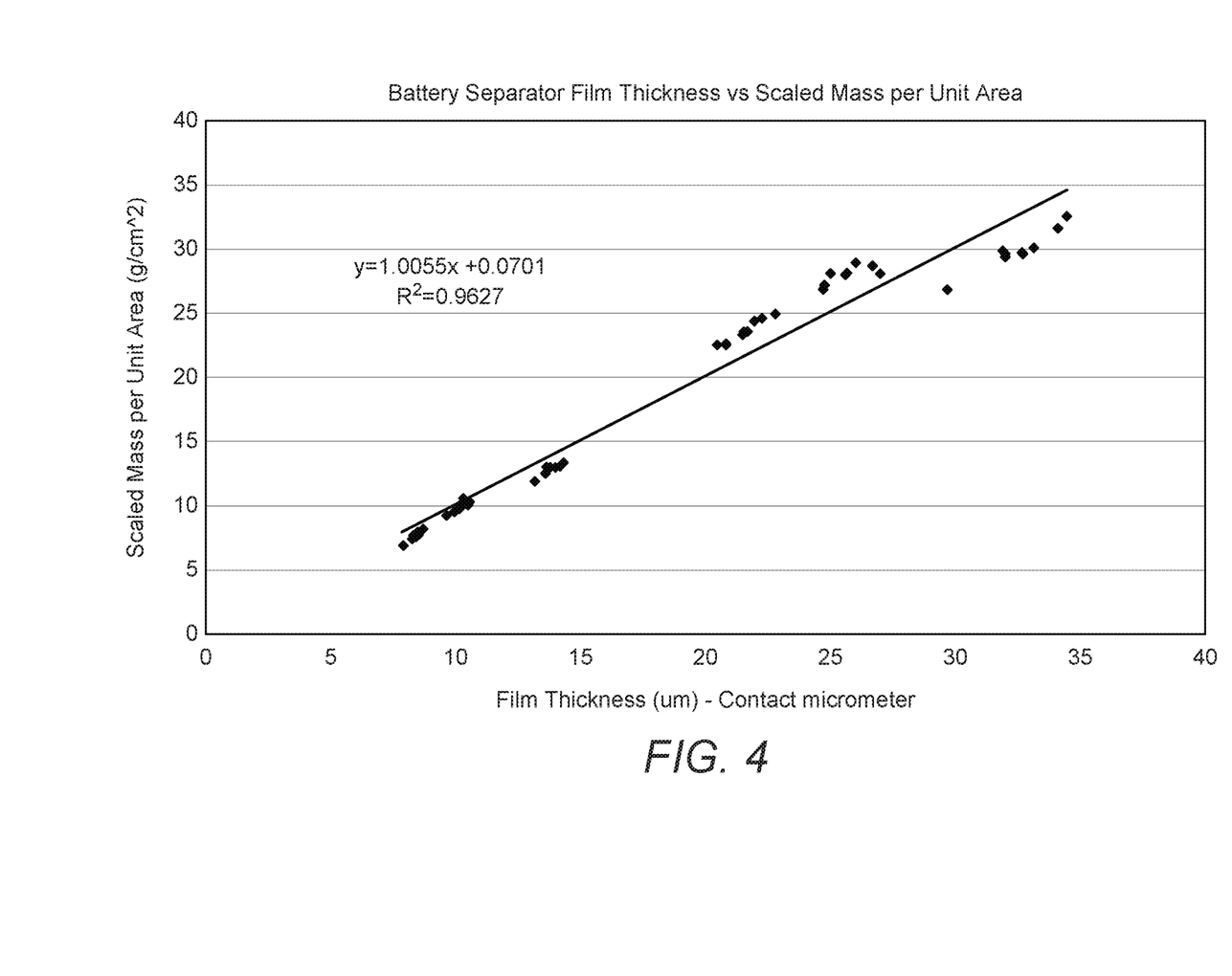
FIG. 4 shows contact micrometer thickness vs. scaled mass per unit area for several samples of example BSF.

FIG. 4 shows a plot of true thickness vs scaled mass per unit area for several samples of BSF. The mass per unit area values were obtained by weighing samples of a fixed area. The values were then scaled by a constant factor. The thickness was measured with a contact micrometer.

As already described, current moving web 'thickness' measurements only measure the mass per unit area of the film and assume that the thickness is linearly related (i.e. the film, has a constant density). FIG. 4 shows that this is not the case for BSF. Even if the mass per unit area measurement is perfect, the scaled mass per unit area inferred 'thickness' measurement will not represent the true thickness.

Figure 5:
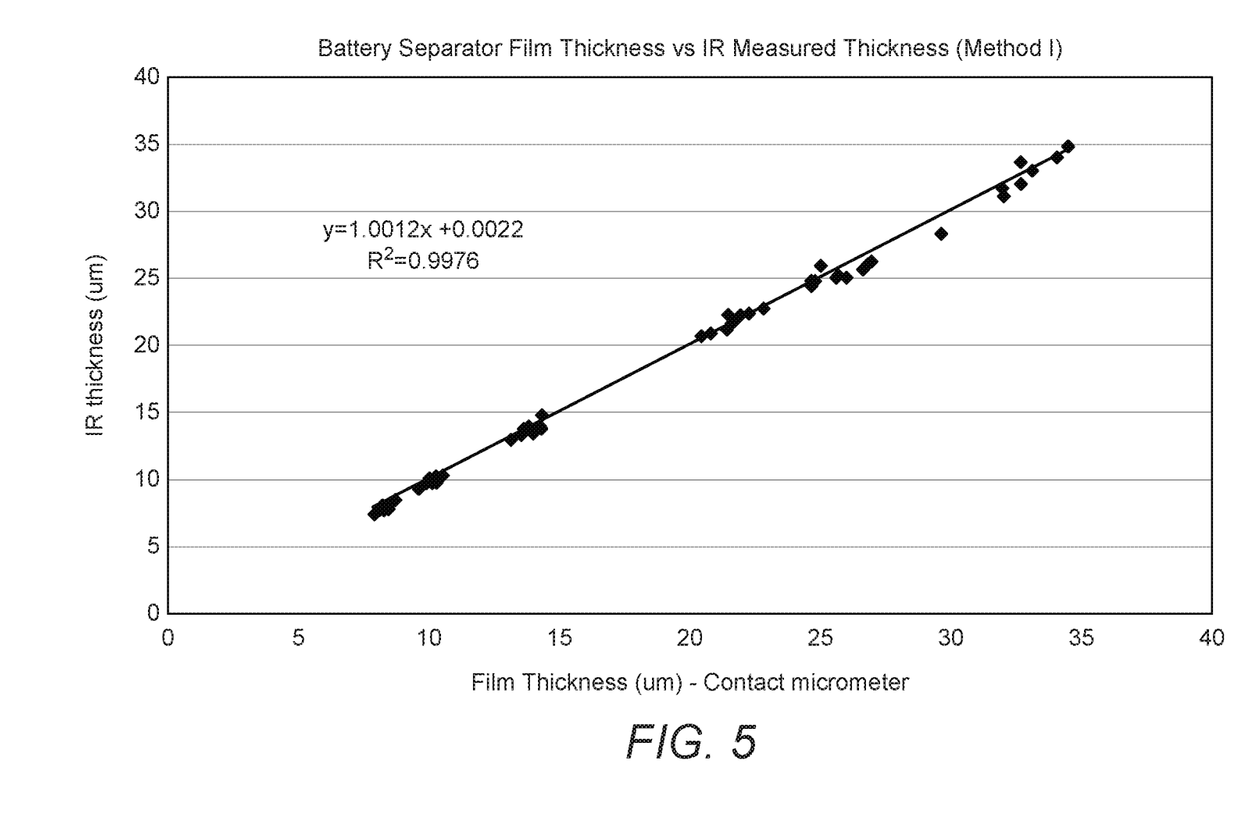
FIG. 5 shows contact micrometer thickness vs. IR measurement obtained by a method in accordance with a first embodiment.
Figure 6:
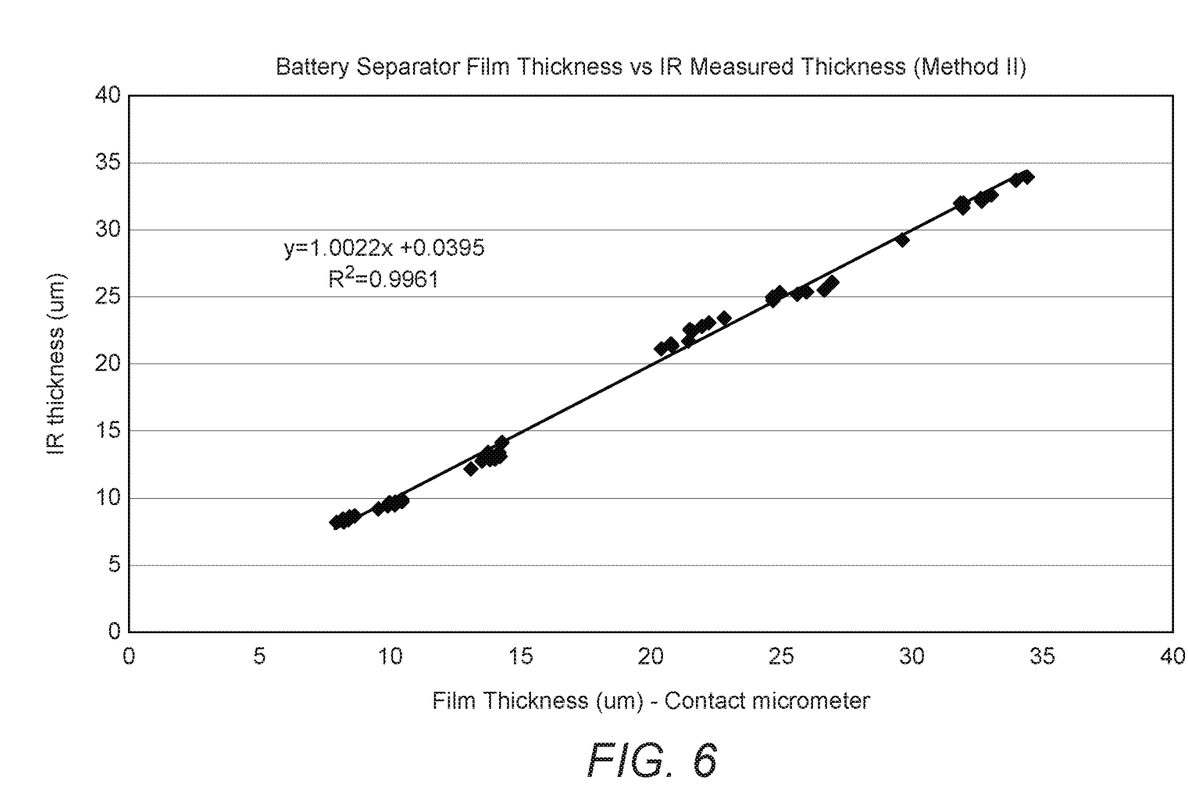
FIG. 6 shows contact micrometer thickness vs. IR measurement obtained by a method in accordance with a second embodiment.

FIGS. 5 and 6 plot our scatter based infrared measurement against the contact micrometer thicknesses, using methods I and II as described above. In both cases, it may be seen that the measurement gives a better measure of the true thickness than the current method for measuring thickness (based on scaling the mass per unit area measurement).

In embodiments, method I and II are also used to measure the density of the BSF, either directly or by combination with a conventional mass per unit area measurement.

In embodiments, the material of interest is a battery separator film, optionally, a lithium-ion battery separator film. However, it may be understood that the method is equally applicable to any porous sample in which a transmission measurement may be made.

Although aspects and embodiments have been described above, variations can be made without departing from the inventive concepts disclosed herein.

The invention claimed is:

1. A method for measuring radiation scattered by a first sample of a material, the method comprising:
   determining a first and second wavelength at which the material exhibits substantially no absorption;
   measuring a transmission of the first sample at the first wavelength;
   measuring a transmission of the first sample at the second wavelength; and calculating, based on the transmissions of the first sample at the first and second wavelengths, a first parameter, S, of the first sample using a first multivariate regression model comprising first regression coefficients, wherein the first parameter is a parameter which affects a total amount of radiation scattered by the first sample at the first and second wavelengths.

2. The method as claimed in claim 1, wherein measuring the transmission of the first sample at the first wavelength comprises illuminating the first sample with incidence radiation including the first wavelength and measuring an intensity of radiation transmitted by the first sample at the first wavelength.

3. The method as claimed in claim 1, wherein:
measuring the transmission of the first sample at the first wavelength comprises filtering radiation at the first wavelength; and
measuring the transmission of the first sample at the second wavelength comprises filtering radiation at the second wavelength.

4. The method as claimed in claim 3, wherein filtering radiation at the first wavelength is performed on at least one of radiation incident on the first sample or radiation transmitted by the first sample at the first wavelength.

5. The method as claimed in claim 3, wherein filtering radiation at the second wavelength is performed on at least one of radiation incident on the first sample or radiation transmitted by the first sample at the second wavelength.

6. The method as claimed in claim 1, wherein measuring the transmission of the first sample at the second wavelength comprises illuminating the first sample with incidence radiation including the second wavelength and measuring an intensity of radiation transmitted by the first sample at the second wavelength.

7. The method as claimed in claim 1, wherein the first and second wavelengths each comprise at least one of a visible wavelength, an infra-red wavelength, a near-infrared wavelength, or a mid-infrared wavelength.

8. The method as claimed in claim 1, wherein at least one of the first wavelength or the second wavelength is a scatter-affected wavelength.

9. The method as claimed in claim 1, wherein an amount of scatter exhibited by the first sample at the first wavelength is different from an amount of scatter exhibited by the first sample at the second wavelength.

10. The method as claimed in claim 1, wherein the first parameter, S, is a parameter related to at least one of a porosity or a density of the first sample.

11. The method as claimed in claim 1, wherein the first multivariate regression model is a first linear multivariate regression model.

12. The method as claimed in claim 1, further comprising:
calculating the first regression coefficients by:
measuring transmissions of a second sample and a third sample of the material at the first wavelength;
measuring transmissions of the second and third samples at the second wavelength;
measuring the first parameter, S, of the second and third samples; and
calculating the first regression coefficients of the first multivariate regression model,
wherein the transmissions of the second sample at the first and second wavelengths are independent variables and the corresponding first parameter measurement of the second sample is a dependent variable of a first equation of the first multivariate regression model, and
wherein the transmissions of the third sample at the first and second wavelengths are independent variables and the corresponding first parameter measurement of the third sample is a dependent variable of a second equation of the first multivariate regression model.

13. The method as claimed in claim 12, wherein:
the first parameter, S, is porosity; and
measuring the first parameter, S, of the second and third samples comprises calculating the porosity of the second and third samples using a formula, $$S=1-(\text{sample density/material density}),$$

wherein the sample density is a density of a sample, measured by dividing a mass per unit area of the sample by sample thickness, and the material density is a known density of a material with no pores.

14. The method as claimed in claim 1, wherein the first and second wavelengths are determined by spectroscopy.

15. The method as claimed in claim 1, further comprising:
calculating a second parameter, A, of the first sample using a second multivariate regression model comprising second regression coefficients, wherein the second parameter is a parameter related to a mass per unit area, $g/m^2$, of the first sample.

16. The method as claimed in claim 15, further comprising:
determining a third wavelength and a fourth wavelength, at which an amount of absorption exhibited by the first sample at the third wavelength is different from an amount of absorption exhibited by the first sample at the fourth wavelength;
measuring a transmission of the first sample at the third wavelength including filtering radiation at the third wavelength; and
measuring a transmission of the first sample at the fourth wavelength including filtering radiation at the fourth wavelength.

17. The method as claimed in claim 16, further comprising:
calculating the second regression coefficients by:
measuring transmissions of a fourth sample and a fifth sample of the material at the third wavelength;
measuring transmissions of the fourth and fifth samples at the fourth wavelength;
measuring the second parameter, A, of the fourth and fifth samples; and
calculating the second regression coefficients of the second multivariate regression model,
wherein the transmissions of the fourth sample at the third and fourth wavelengths are independent variables and the corresponding second parameter measurement of the fourth sample is a dependent variable of a first equation of the second multivariate regression model, and
wherein the transmissions of the fifth sample at the third and fourth wavelengths are independent variables and the corresponding second parameter measurement of the fifth sample is a dependent variable of a second equation of the second multivariate regression model.

18. The method as claimed in claim 17, wherein the second parameters of the fourth and fifth samples are measured by weighing samples of a predetermined area.

19. The method as claimed in claim 16, wherein at least one of the third or fourth wavelength is the same as at least one of the first or second wavelength.

20. The method as claimed in claim 16, wherein at least one of the fourth or fifth sample is the same as at least one of the second or third sample.

21. The method as claimed in claim 16, wherein the first parameter, S, is used as a scatter-correction factor for the transmission measurements at the third and fourth wavelengths.

22. The method as claimed in claim 15, the method further comprising:
    combining the calculated first parameter, S, of the first sample with the calculated second parameter, A, of the first sample to calculate at least one of a thickness, a mass per unit area, a density, or a porosity of the first sample.

23. The method as claimed in claim 22, wherein combining the calculated first parameter, S, of the first sample with the calculated second parameter, A, of the first sample comprises multiplication or division.

24. The method as claimed in claim 22, wherein combining the calculated first parameter, S, with the calculated second parameter, A, comprises calculating at least one of the thickness, the mass per unit area, the density or the porosity (T) of the first sample using an equation selected from the group comprising:

$$T=a[(Sb+c)(Ad+e)]+f;$$

$$T=a[(Sb+c)/(Ad+e)]+f;$$

$$T=a[(Ad+e)/(Sb+c)]+f; \text{ and}$$

$$T=a\{A[(Sb)+c]\}+d$$

wherein a, b, c, d, e and f are empirically-calculated constants.

25. The method as claimed in claim 1, wherein the material is at least one of a battery separator film or a lithium-ion battery separator film.

26. A method, for measuring a first sample of a material, comprising:
    calculating a first parameter, S, of the first sample of the material by:
        determining a spectrum for the material associated with an absorption by the material to radiation;
        obtaining a transmission of the first sample at the determined spectrum;
        determining, based on the transmission of the first sample, scatter correction parameters for the first sample using a scatter correction model;
        using the scatter correction parameters to calculate the first parameter, S;
    calculating a second parameter, A, of the first sample, wherein the second parameter is a parameter related to a mass per unit area of the first sample; and
    combining the calculated first parameter, S, of the first sample with the calculated second parameter, A, of the first sample to calculate at least one of a thickness, the mass per unit area, a density, or a porosity of the first sample.

27. The method as claimed in claim 26, wherein determining the spectrum for the material comprises at least one of:
    averaging measured spectra of a plurality of samples of the material; or
    employing a rolling time average measurement of the spectrum measured on a moving sample of the material.

* * * * *